United States Patent [19]

Bozal Gonzalez

[11] 4,201,219
[45] May 6, 1980

[54] CARDIAC PACE-MAKER

[76] Inventor: José L. Bozal Gonzalez, C/Tilos, 30 - Urbanizacion Montecarlos, Pozuelo de Alarcon, (Madrid-23), Spain

[21] Appl. No.: 883,251

[22] Filed: Mar. 3, 1978

[30] Foreign Application Priority Data

Mar. 3, 1977 [ES] Spain .............................. 226.859[U]

[51] Int. Cl.$^2$ .............................................. A61N 1/36
[52] U.S. Cl. .............................. 128/419 PG; 128/642
[58] Field of Search ................... 128/419 PG, 2.06 E, 128/2.1 E; 639/2.4; 642/260

[56] References Cited

U.S. PATENT DOCUMENTS

| | | | |
|---|---|---|---|
| 3,593,718 | 7/1971 | Krasner et al. | 128/419 PG |
| 3,650,277 | 3/1972 | Sjostrand et al. | 128/419 C |
| 3,826,244 | 7/1974 | Salcman et al. | 128/2.1 E |
| 4,009,721 | 3/1977 | Alcidi | 128/419 PG |

OTHER PUBLICATIONS

Parker et al. "Electroencephalography and Clinical Neurophysiology" vol. 35, No. 6, Dec. 1973, pp. 647–651.

*Primary Examiner*—William E. Kamm
*Attorney, Agent, or Firm*—Wenderoth, Lind & Ponack

[57] ABSTRACT

The rhythm of a cardiac pace-maker is controlled by regulation signals detected in the nerves via receivers. At least one neurodetector device detects trains of nerve impulses and/or the action potentials which circulate through the nerves via, or which are generated in, the nerve receivers and converts them into electric signals. Associated electric circuits transform the electric signals detected in the neurodetectors and process the same so that the frequency of the periodic impulse generator of the pace-maker is modified.

3 Claims, 13 Drawing Figures

CARDIAC PACE-MAKER

BACKGROUND OF THE INVENTION

The present invention relates to a cardiac pace-maker having a rhythm controlled by regulation signals detected in the nerves, in receivers, or in both simultaneously.

The heart has an impulse conduction system which permits the synchronization of all the fibers of the cardiac muscle. The sinus nodule is the initiator of the heart beat and, therefore, the main natural pace-maker.

In recent years the use of cardiac pace-makers in those patients, whose hearts have lost the capacity of maintaining the rhythm and synchronism necessary between its parts to pump blood efficiently, has been generalized.

A cardiac pace-maker is a device which supplies, rhythmically, electrical impulses to the cardiac muscle, forcing the heart to beat with the rhythm imposed, electronically replacing the natural electric excitation.

There are, at present, three types of pace-makers: asynchronous or fixed rhythm units which give a fixed frequency of beats, synchronous units which adjust the rhythm to that of the auricular contraction when the same is present, and finally units which operate on request and which are inhibited when the presence of natural QRS complex is detected.

The main disadvantage of present-day pace-makers is that they lack the capacity to regulate their rhythm, depending on the biological needs imposed on the patient in each of various activities.

A normal heart regulates its rhythm with the purpose of supplying blood to the tissues, depending on the needs thereof, by means of nerve circuits whose afferent via depart from the nerve receivers, baro receivers, chemoreceivers, etc., and whose efferent via act on the natural cardiac pace-makers, the sinus nodule, the atrioventricular nodule, etc.

A conventional cardiac pace-maker is an electronic device comprising a periodic impulse generator which should have a pre-determined shape for its maximum efficiency, fed by a battery and connected to the myocardium by an electrode and its connecting cable. However, this electronic simplicity is counterbalanced by the following disadvantages. Protecting encapsulation of the electronic circuit must be made from a biocompatible material. The environment into which the pace-maker is installed is tremendously aggressive for its components, thus its average life is remarkable reduced. The mercury batteries are affected by the moisture caused by the growth of metal dendrites and, consequently, by short circuits. It has been remarkably improved due to techniques of encapsulation.

The battery is a key element for the average life of the pace-maker. Conventional batteries are of mercury-zinc oxide whose average life is of about 33 months. Use is now being made of lithium batteries, in a solid state, wherein the anode is of lithium and the cathode of iodide, generating electricity by the migration of the lithium ions through the salt. It does not generate gas and can be hermetically encapsulated, which, together with its greater density in energy, assures an average life which is expected to exceed five years.

Another battery presently used employs Plutonium 238 whose radiation is utilized in a thermocell to generate electricity. Its expected average life is more than 10 years, its cost being two or three times that of lithium batteries.

Active research is being undertaken to obtain new sources of energy, especially utilizing electrochemical sources within the human body.

Another disadvantage resides in the stimulation electrode and the connecting cable. The main problems arise from the need of an effective fastening of the electrode which prevents displacements and of the security that the connecting cable does not break due to wear since it is subjected to continuous bending stresses.

SUMMARY OF THE INVENTION

The object of this invention is to provide a system which permits the making of a cardiac pace-maker having a variable rhythm controlled by regulation signals detected in the nerve receivers and/or via of the heart.

The cardiac rhythm is automatically regulated according to the particular activity of the patient, the detection of the biological needs being effected in the nerve receivers or via themselves.

The pace-maker of the invention is a conventional pace-maker from the point of view of the periodic impulse generator, encapsulation, batteries, the cable and myocardial excitation electrode. The novel feature of the invention involves a detector in the nerve receivers and/or via and the associated electronic circuits which convert the detected nerve impulses into modifying signals of the frequency of the periodic impulse generator and, consequently, of the cardiac rhythm.

The neurodetector is, in principle, any physical system capable of detecting the trains of nerve impulses and/or the action potentials which circulate through the afferent or efferent nerve vias or which are generated in the cardio-vascular-pulmonar regulating nerve receivers, and of converting them into electric signals.

The associated electronic circuits are devices which convert the electric signals which appear in the neurodetectors and combine them so that they modify the frequency of the periodic impulse generator of the pace-maker.

BRIEF DESCRIPTION OF THE DRAWINGS

To complement the description which will subsequently be made and for a better understanding of the characteristics of the invention, reference is made to the accompanying drawings wherein.

DETAILED DESCRIPTION OF THE INVENTION

To simplify this description, reference will be made to an embodiment having a single neurodetector in the sinus carotid applied in the joint of a Hering nerve, although it should be understood that this is not limitative of the scope of this invention which may include any number of neurodetectors applicable to their corresponding cardio-vascular-pulmonary regulating nerve receivers or via any points of the paths thereof.

Figure 1:
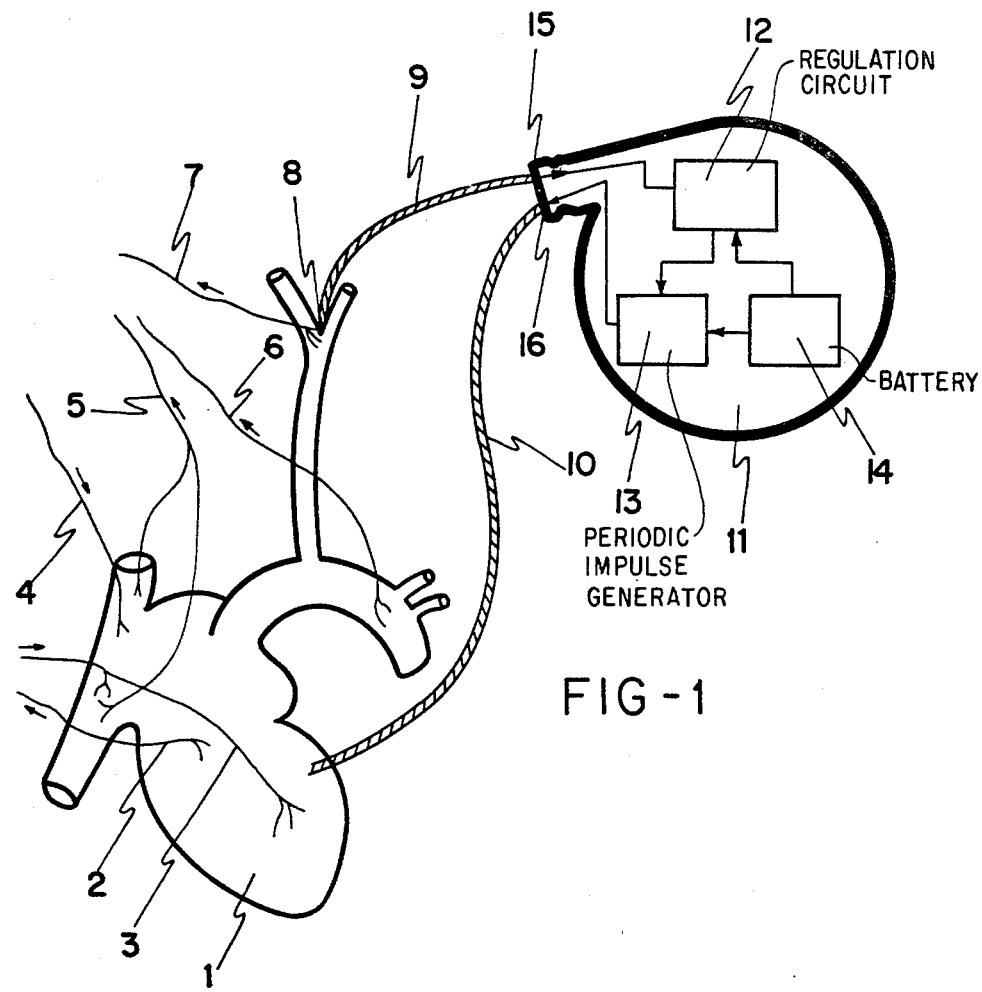
FIG. 1 is a general schematic view of the system in accordance with the present invention.

FIG. 1, corresponding to a general view of the system, illustrates the heart and its main vessels 1, the afferent fibers 2 of the spinal cord, the fibers 3 of the sympathetic nervous system, the efferent fibers 4 of the lazy nerve, the afferent fibers 5 of the right auricle and of the caval vein, the afferent fibers 6 of the lazy vein and the afferent fibers 7 of the sinus and glomus carotids.

The position of the glomus carotid at the carotid branching point has been referenced as 8, and a neurodetector 9 is applied to the glomus carotid and is connected, by means 15, to the body of a pace-maker 11.

An excitation electrode 10 is connected, by means 16, to the body of the pace-maker, in the interior of which a regulation circuit 12 is connected to a periodic impulse generator 13, both elements being fed by a battery 14.

In the interior of the body of the pace-maker 11, the neurodetector 9 is connected to the regulation circuit 12, where the direction of the arrow indicates the informative flow inwards.

Likewise, the impulse generator 13 is joined to the excitation electrode 10, where the direction of the arrow indicates the direction in which the impulses move.

Figure 8:
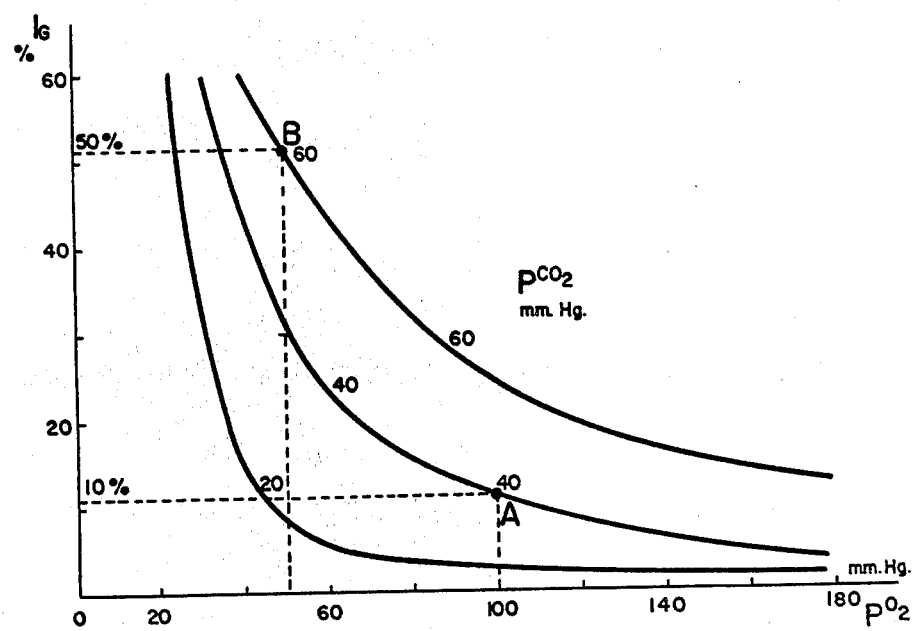
FIG. 8 is a diagram of the correlation between partial pressures of oxygen and carbon dioxide in the glomus carotid and the number of impulses per second detected, also illustrating the cases contemplated in FIGS. 5 and 6.

The neurodetector 9, which comprises in this case a microelectrode connected to a cable, detects the train of nerve impulses generated in the sinus and glomus carotids which appear in the Hering nerve and which are lead towards the regulation circuit 12 where they are filtered, the average density of the train of impulses is calculated and a modifying electric voltage of the frequency of the periodic impulse generator 13 is generated according to the cardiac rhythm necessary for the arterial pressure values $pO_2$ and $pCO_2$ represented in FIG. 8.

The periodic impulse generator 13 furthermore shapes the impulse which supplies the excitation to the electrode 10.

Figure 2:
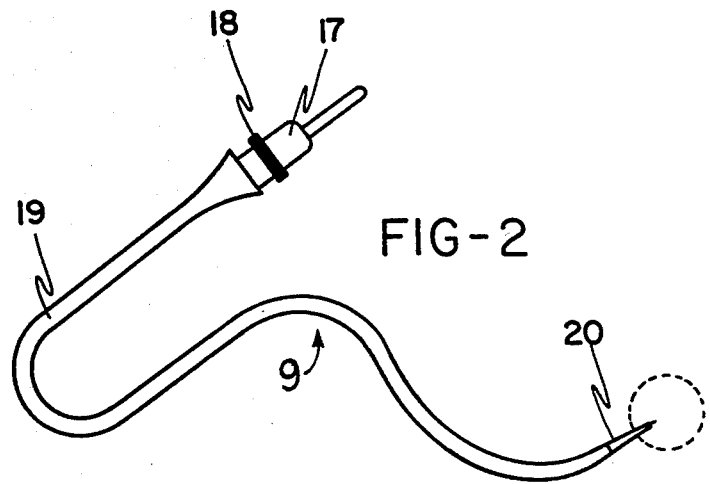
FIGS. 2, 3 and 4 are respectively schematic views of one possible embodiment of a bipolar neurodetector and details of key elements thereof.

FIG. 2 illustrates in more detail the structure of the neurodetector 9 as including a connector 17 for connection to the body of the pace-maker by a fastening device 18. A conductor cable 19 is formed of fibers of a good conductor material interlocked to obtain a good flexibility enclosed in a biocompatible silicone rubber. The neurodetector 9 has an end 20 at which is arranged the microelectrode.

Figure 3:
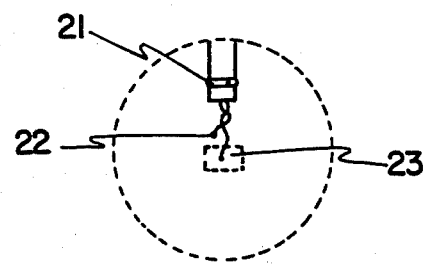
Figure 4:
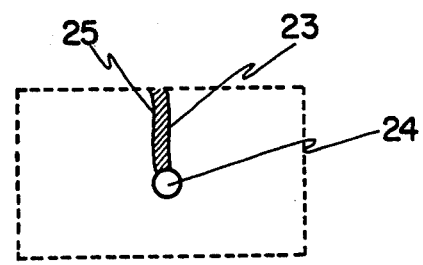

This end of the neurodetector 9 is enlarged in the detail of FIG. 3, which illustrates a transverse orifice 21 which permits the passage therethrough of a fastening wire, and the microelectrodes 22 and 23, one of which is enlarged in the detail of FIG. 4 and is shown therein as including a silver end ball 24 and a Teflon insulating casing 25. These microelectrodes are readily manufactured, the diameter of the silver ball being of about ½ mm.

Figure 5:
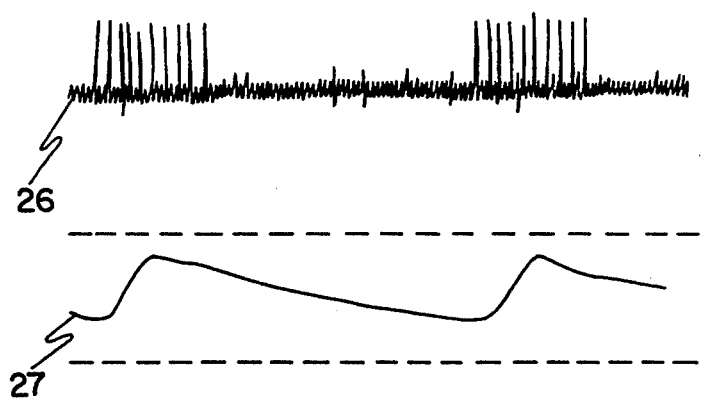
FIGS. 5 and 6 are graphs illustrating the shapes of trains of impulses detected, in different physiological conditions, by the neurodetector.

The signals detected by the neurodetector are shown at 26 in FIG. 5 and correspond to the trains of impulses which appear in the Hering nerve when atmospheric air is breathed in by a healthy person at normal $pO_2$ and $pCO_2$ values.

The synchronous arterial pressure curve with the train of nerve impulses is shown at 27. The impulses having a greater amplitude correspond to the action potentials of the baroreceivers of the sinus carotid which, as can be seen, appear in the peaks of arterial pressure.

The impulses having a smaller amplitude and a higher frequency are those corresponding to the action potentials of the chemoreceivers of the glomus carotid.

Figure 6:
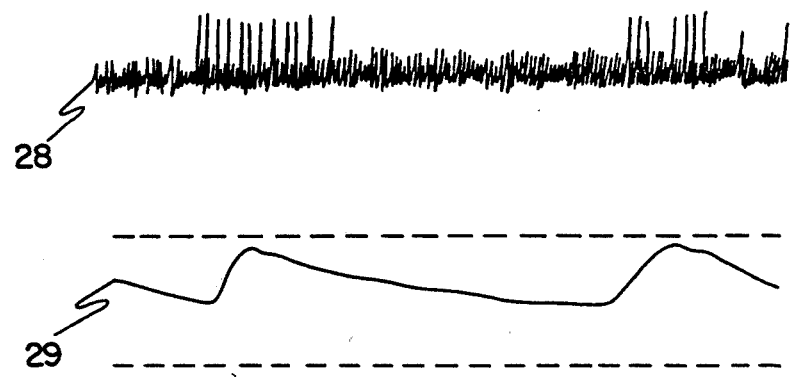

FIG. 6 represents the same graphs as FIG. 5 but when breathing in a mixture poor in oxygen. Thus, curves 28 and 29 of FIG. 6 correspond to curves 26 and 27 of FIG. 5.

It can be seen that the lack of oxygen, and therefore the low $pO_2$, produces a remarkable increase in the frequency of the impulses due to the chemoreceivers.

Figure 7:
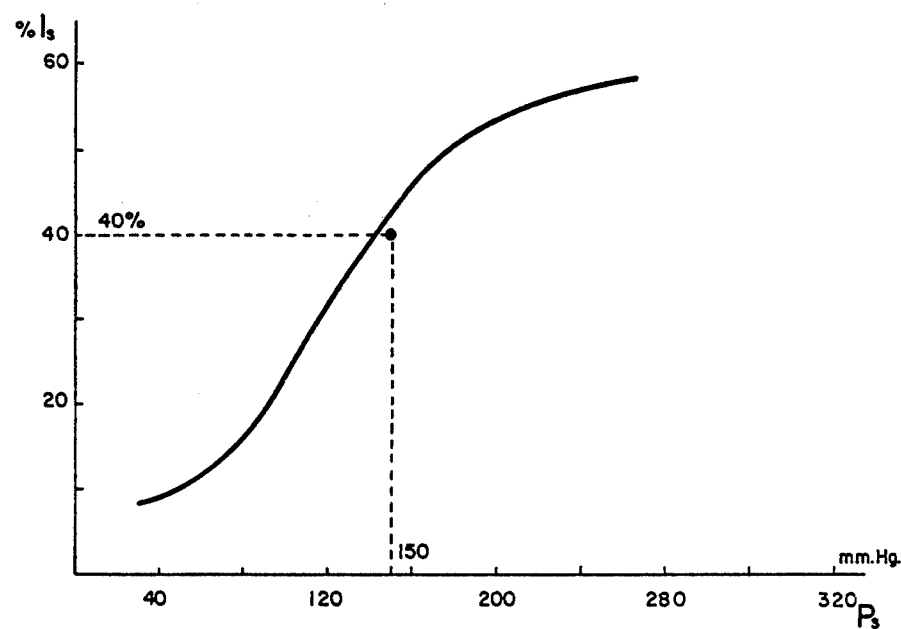
FIG. 7 is a diagram of the correlation between the arterial pressure in the sinus carotid and the number of impulses per second detected, illustrating the application for the cases contemplated in FIGS. 5 and 6.

A graphic representation of the variation in the average frequency of the impulses which appear in the neurodetector coming from the excitation of the sinus carotid, depending on the arterial pressure (Ps) therein, is shown in FIG. 7.

The pressure, in millimeters of mercury in the sinus, has been represented in the abscissa, while the percentage of impulses per second with relation to the maximum possible has been represented in the ordinate.

The point indicated in the curve, having an abscissa value of 150 mm Hg and an ordinate value of 40%, corresponds to the positions described in FIGS. 5 and 6.

A graphic representation of the variation in the average frequency in the impulses which appear in the neurodetector coming from the excitation of the glomus carotid, depending on the $pO_2$ and $pCO_2$ in the blood, is shown in FIG. 8.

This graph represents, in the abscissa, the $pO_2$ in mm. of mercury, while the percentage of impulses per second with relation to the maximum possible is represented in the ordinate.

Likewise, there is represented a plurality of curves, depending on various $pCO_2$ values.

Point A indicated in the graph at an abscissa value of 100 mm. of mercury and an ordinate value of 10%, at a $pCO_2$ value of 40 mm. Hg., corresponds to the case described with reference to FIG. 5 wherein atmospheric air is breathed in and the $pO_2$ and $pCO_2$ compositions are normal, producing a low level of impulses per second.

Point B indicated in the same graph at an abscissa value of 50 mm. Hg and an ordinate value of 50%, at a $pCO_2$ value of 60 mm. Hg., corresponds to the case described with reference to FIG. 6 wherein a mixture poor in oxygen has been breathed in and wherein the $pO_2$ composition has been reduced and the $pCO_2$ composition has been increased, thus giving rise to a high level of impulses per second.

These graphs are merely explanatory of the behavior of the sinus and glomus carotids and of the correlation existing between detected impulses and the physiological conditions of the patient insofar as arterial pressure (Ps) and the partial pressure combination of oxygen (pO$_2$) and carbon dioxide (pCO$_2$) which, as is known, has a compensatory effect in the dissociation curves of the oxyhaemoglobins.

It can clearly be seen from the aforegoing that the number of impulses per second detected by the neurodetector and classified into the two types, coming from the sinus carotid and from the glomus carotid, supply the necessary information with respect to the physiological condition of the patient.

Figure 9:
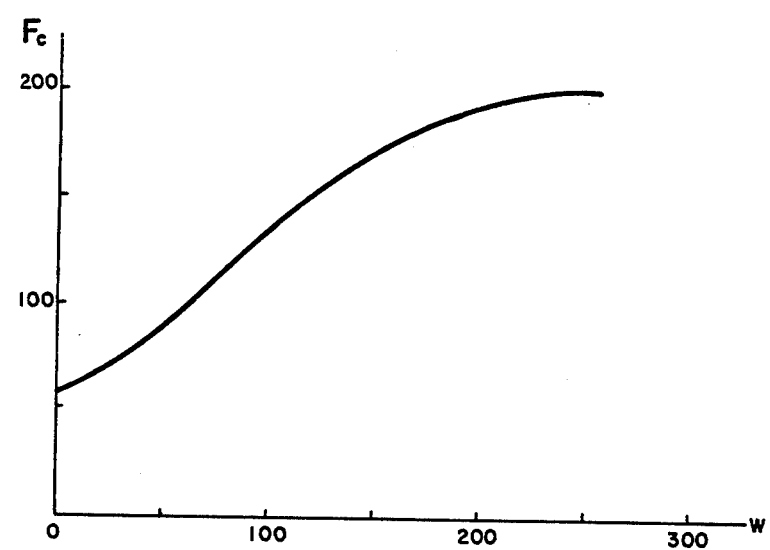
FIGS. 9, 10 and 11 are respectively graphs illustrating variations in the cardiac frequency, maximum arterial pressure and partial pressures of oxygen and carbon dioxide in the artery, depending on the physical work done.

FIG. 9 is a graph of the relationship between the cardiac frequency (Fc) and the physical work (W) in a normal heart. This diagram illustrates the manner in which the heart responds by increasing its cardiac rhythm in response to a greater demand for oxygen caused by the need of the tissues to adapt themselves to stress.

Figure 10:
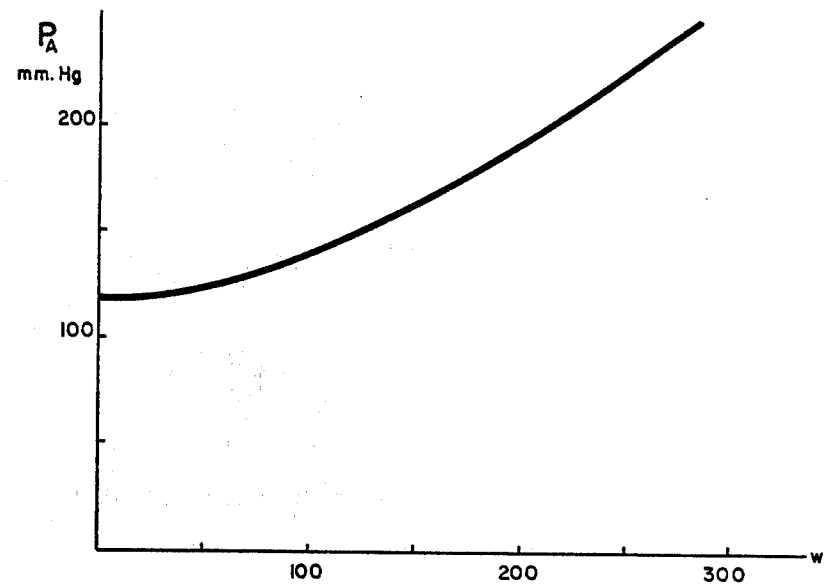

FIG. 10 is a graph of the variation in the maximum arterial pressure (P$_A$), depending on the physical work (W). The fact that the arterial pressure increases as the physical stress increases, is illustrated.

Figure 11:
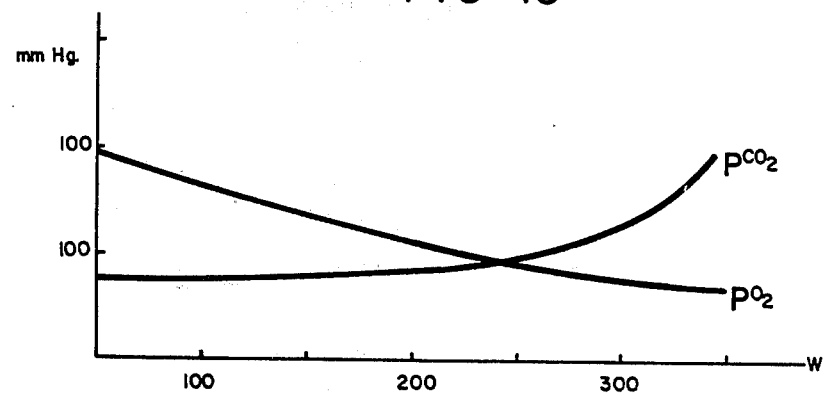

FIG. 11 is a graph of the variation in the partial pressure of oxygen and carbon dioxide (pO$_2$ and pCO$_2$) in the artery, depending on the physical work (W).

When the physical stress increases, the pO$_2$ decreases and the pCO$_2$ increases. While this stress is moderate, the variations are slight, especially the variation in the pCO$_2$, but when the stress exceeds the capacity of oxygenation, great variations in the partial pressures are produced. In the first portions of the graph the regulation mechanism which prevent mayor changes acts.

The correlations necessary between the physical work (W), the cardiac rhythm (Fc), the maximum arterial pressure (P$_A$), the partial pressure of oxygen (pO$_2$), the partial pressure of the CO$_2$ (pCO$_2$), the impulses per second in the sinus cortid (I$_s$), and finally the impulses per second in the glomus cortid (I$_g$) are clearly established from the above described graphs.

Figure 12:
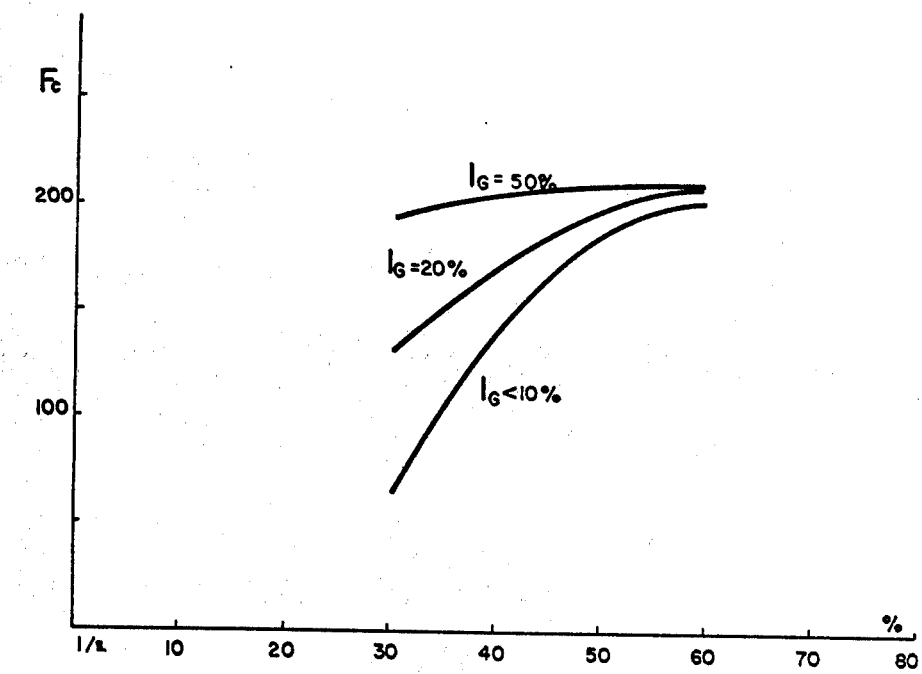
FIG. 12 is a graph of the relationship between the cardiac frequency and the impulses per second detected by the neurodetector.

From this assembly of graphs, the graph of FIG. 12 has been obtained, which illustrates the manner in which the cardiac frequency (Fc) varies, depending on the impulses in the sinus carotid and the glomus carotid. FIG. 12 therefore represents the behavior of the neuroregulated cardiac pace-maker and, thus, the function of the regulation circuits.

This complete assembly of graphs of FIGS. 5, 6, 7, 8, 9, 10, 11 and 12 is merely indicative as to values of magnitude and tendencies and can be modified without affecting the scope of this invention.

Figure 13:
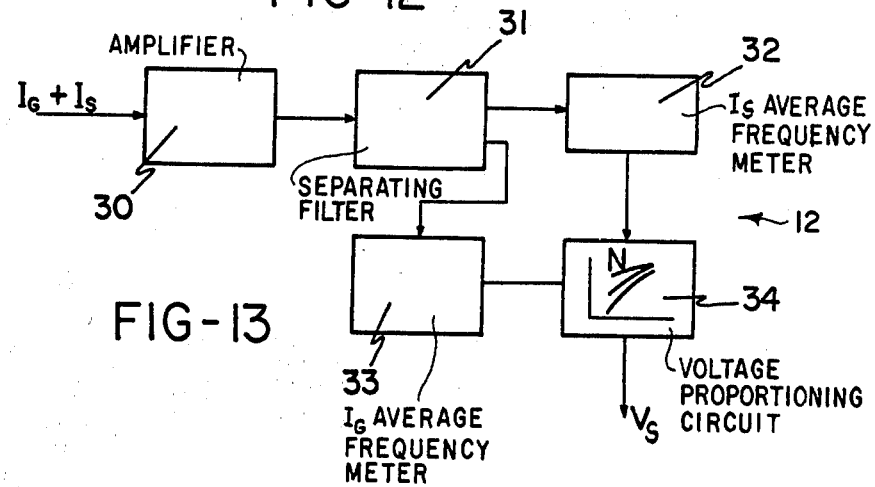
FIG. 13 is a schematic diagram of the various electronic elements of the regulation circuit.

FIG. 13 illustrates an embodiment of the electronic components of the regulation circuit 12 necessary to modify the frequency of the impulses of the generator 13 of the pace-maker.

The signal of the neurodetector 9 is amplified by the amplifier 30 from where it passes to the separating filter 31 at whose outlet there are obtained, separately, the impulses of the sinus carotid and the glomus carotid, whose average frequencies are calculated by the meters 32 and 33, respectively, and both signals are lead to a circuit 34 which proportions a voltage v$_s$ which is proportional to the desired cardiac frequency, according to the graph of FIG. 12.

This voltage V$_s$, proportional to the desired cardiac frequency, modifies the frequency of the periodic impulse generator 13.

The aforegoing, set forth in this example, can be applied and/or extended to other nerve receivers with obvious necessary modifications of the curves and graphs.

Likewise, the concept of the invention is perfectly applicable when using the efferents as the detection source, which modification is of great interest.

I claim:

1. A cardiac pace-maker comprising:
   neurodetector means, connectable to nerve vias or receivers in the heart of a patient, for detecting a train of nerve impulses therein and for converting such detected train of nerve impulses into electrical signals representative of physiological activity of the heart of the patient;
   periodic impulse generator means for supplying electrical impulses to the heart of the patient; and
   regulation circuit means, connected to said neurodetector means and to said periodic impulse generator means, for generating a modifying signal proportional to the cardiac frequency necessary for the physiological activity of the heart as a function of said electrical signals, for supplying said modifying signal to said periodic impulse generator means, and for thereby modifying the frequency of said electrical impulses from said periodic impulse generator means to correspond to said necessary cardiac frequency.

2. A cardiac pace-maker as claimed in claim 1, wherein said neurodetector means comprises microelectrode means for detecting a train of nerve impulses generated in the sinus and glomus carotids of the heart, and said regulation circuit means comprises an amplifier for receiving and amplifying said train of impulses from said microelectrode means, separating filter means for separating the said impulses from said sinus carotid and from said glomus carotid, first and second meters for calculating the average frequencies of said impulses from said sinus and glomus carotids, respectively, and for generating signals representative thereof, and voltage proportioning means for converting said representative signals into said modifying signal.

3. A cardiac pace-maker as claimed in claim 2, wherein said microelectrode means comprises first and second microelectrodes, each including a silver ball detector end and a Teflon coated casing.

* * * * *